(12) United States Patent
Hayes et al.

(10) Patent No.: US 6,338,312 B2
(45) Date of Patent: Jan. 15, 2002

(54) INTEGRATED ION IMPLANT SCRUBBER SYSTEM

(75) Inventors: Michael W. Hayes, San Jose; Mark R. Holst, Concord, both of CA (US); Jose I. Arno, Brookfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 09/060,675

(22) Filed: Apr. 15, 1998

Related U.S. Application Data

(63) Continuation-in-part of application No. 08/785,342, filed on Jan. 17, 1997, now Pat. No. 5,827,947.

(51) Int. Cl.[7] .......................... C23C 16/00; B01D 53/34
(52) U.S. Cl. ........................ 118/723 CB; 118/723 R; 423/210; 423/240 S
(58) Field of Search ................. 118/723 CB, 723 R; 423/210, 240 S

(56) References Cited

U.S. PATENT DOCUMENTS

| | | | |
|---|---|---|---|
| 4,936,877 A | | 6/1990 | Hultquist et al. |
| 4,996,030 A | * | 2/1991 | Kitahara et al. |
| 5,138,869 A | | 8/1992 | Tom |
| 5,325,705 A | | 7/1994 | Tom |
| 5,512,262 A | * | 4/1996 | Shimada et al. |
| 5,518,528 A | * | 5/1996 | Tom et al. |
| 5,583,282 A | | 12/1996 | Tom |
| 5,704,965 A | | 1/1998 | Tom et al. |
| 5,704,967 A | | 1/1998 | Tom et al. |
| 5,707,424 A | | 1/1998 | Tom et al. |
| 5,731,510 A | * | 3/1998 | Jones et al. |
| 5,756,060 A | * | 5/1998 | Otsuka et al. |
| 5,795,356 A | * | 8/1998 | Leveen |
| 5,827,947 A | * | 10/1998 | Miller et al. |
| 5,851,293 A | * | 12/1998 | Lane et al. |
| 5,853,678 A | * | 12/1998 | Sugimori et al. |
| 5,856,676 A | * | 1/1999 | Rheem et al. |
| 5,882,366 A | * | 3/1999 | Holst et al. |

\* cited by examiner

Primary Examiner—Deborah Jones
Assistant Examiner—Jennifer McNeil
(74) Attorney, Agent, or Firm—Steven J. Hultquist; Robert A. McLauchlan; Oliver A. Zitzmann

(57) ABSTRACT

An ion implantation process system, including an ion implanter apparatus for carrying out an ion implantation process. A supply of source gas for the ion implantation process is arranged to flow to the ion implanter apparatus, which discharges an effluent gas stream including ionization products of the source gas during the ion implantation process. The system includes an effluent abatement apparatus for removing hazardous effluent species from the effluent gas stream. The source gas may be furnished from a low pressure gas source in which the source gas is sorptively retained in a vessel on a sorbent medium having affinity for the source gas, and desorbed for dispensing to the process system. A novel scrubbing composition may be employed for effluent treatment, and the scrubbing composition breakthrough of scrubbable component may be monitored with a device such as a quartz microbalance monitor.

23 Claims, 5 Drawing Sheets

INTEGRATED ION IMPLANT SCRUBBER SYSTEM

This application is a continuation-in-part of U.S. patent application Ser. No. 08/785,342, filed Jan. 17, 1997 and issued Oct. 27, 1998 as U.S. Pat. No. 5,827,947.

BACKGROUND OF THE INVENTION

1. Field of the Invention

This invention relates generally to an integrated system for ion implantation and scrubbing treatment of the resulting ion implantation effluent for abatement of selected components therein, e.g., components which are hazardous or otherwise undesirable in the effluent stream discharged from the ion implant chamber.

2. Description of the Related Art

Ion implantation is progressively widely used for the introduction of dopant species into substrates for the manufacturing of semiconductor device structures.

The increasingly high levels of microelectronic device integration require shallow junction depths and low temperature process conditions, which are well accommodated by ion implantation. Ion implantation provides a high degree of control and reproducibility, and the ability to incorporate the dopant species into buried substrate regions of the microelectronic device structure.

Typical dopant species for silicon-based microelectronic applications include boron as a p-type dopant, and phosphorus, arsenic and antimony as n-type dopants. Silicon, germanium and oxygen are also used as dopant species in some applications. Dopant species are typically formed from source gases, such as boron trifluoride, arsine, boron trichloride, and phosphine, which entail significant safety and handling issues.

The dopant source gases are introduced to an ionizer where the high voltage arc discharges are employed to form a mixture of ionized species of the source gas. Magnetic field separation is employed for the subsequent separation of the specific ionic species to be implanted, which are then accelerated, focused and directed by a scanner mechanism in an ion beam onto the substrate to be implanted, to introduce the implant species into the crystal lattice of the substrate material being bombarded by the ion beam.

Ion implanters typically use $BF_3$, $AsH_3$ and $PH_3$ as primary dopant gases. Other gases, such as $SiF_4$, $Ge_4$, etc. are also used.

Due to the hazardous character of these commonly used dopant gases, significant safety issues are raised. The dopant gases are supplied in conventional practice from high pressure gas cylinders. There is thus a substantial safety threat posed by the danger of leakage of the dopant source gas from the high pressure cylinder, or rupture of the cylinder in use.

The effluent from the ion implantation system thus contains the aforementioned source gases used in the specific application, as well as their ionization decomposition products. Due to their toxicity and hazardous character, it is generally desirable to scrub the effluent gas from the ion implant operation to remove such gases and decomposition products.

The effluent scrubbing operation can be carried out using a variety of wet and/or dry scrubbing operations.

Wet scrubbing of the effluent stream involves contacting the effluent gas from the ion implantation system with a scrubbing liquid to cause the undesired effluent stream components to be absorbed by the liquid, or to react with the liquid (e.g., a caustic solution for contacting with an acid gas effluent) to effect removal of the undesired components from the gas phase.

Dry scrubbing involves contacting the effluent gas with a solid material which functions to chemisorb or react with the undesired components to effect their removal.

In general, wet scrubbing requires the consumption of significant chemical reagents, and thus is less preferred than dry scrubbing, in which a bed of solid-phase scrubbing materials is employed, through which the ion implantation effluent gas is flowed.

It is important to note that for dry scrubbing purposes, the chemical requirements to scrub acid gases such as $BF_3$ and $SiF_4$ are entirely different than the chemical requirements to scrub hydride gases such as $AsH_3$, $PH_3$ and $GeH_4$.

Available data show that $BF_3$ passes through an ion implanter largely intact, $PH_3$ is largely broken down to its elements while passing through the ion implanter, and $AsH_3$ is broken down to a moderate level while passing through the implanter.

It is expected that other fluorinated acid gases will behave similarly to $BF_3$ and pass through an ion implant system largely intact. Thus, the large flowrates of intact acid gas dopants mandate effluent stream treatment for removal of acid gases. While hydride source gases pass through only moderately intact, their high toxicity and low levels of permissible personnel exposure (for example, the threshold limit value (TLV) for $AsH_3$ is 0.05 ppm, or a IDLH of 3 ppm) mandate abatement. Thus, the scrubber employed for treatment of the ion implantation system effluent gas must be capable of handling both acid gases and hydride gases. Such scope of scrubbing utility is difficult to achieve with a single dry scrubbing composition. Multiple beds of different dry scrubbing compositions, split beds of different dry scrubbing compositions, and dry scrubbing composition blends can be used, but these approaches all suffer from the deficiency of being cumbersome in their application and use.

In addition to the foregoing issues incident to the use and operation of ion implantation systems, empirical characterization of ion implant process exhaust streams reveal significant emissions of hazardous gases in the process system from source gas pumps, roughing pumps and from cryogenic pump regeneration cycles.

It would therefore be a significant advance in the art, and accordingly is an object of the present invention, to provide an ion implantation system which eliminates or at least ameliorates the aforementioned hazards of conventional ion implantation processes.

It is another object of the invention to provide an improved system for the treatment of ion implantation process effluents.

Other objects and advantages will be more fully apparent from the ensuing disclosure and appended claims.

SUMMARY OF THE INVENTION

The present invention relates generally to an ion implantation process system having an improved safety character relative to ion implantation process systems of the prior art.

In one aspect, the invention relates to an ion implantation process system, comprising a supply of source gas for the ion implantation process, joined in flow communication with an ion implanter apparatus, with the ion implanter apparatus discharging an effluent gas stream to an effluent abatement apparatus, for removing hazardous effluent species from the effluent gas stream.

The invention in a preferred embodiment includes an ion implantation process system in which the effluent abatement apparatus is positioned in the ion implanter apparatus as a unitary and integrated process arrangement.

In another embodiment, such integrated ion implantation process system further comprises the source gas supply in the integrated arrangement, with the source gas supply, ion implanter apparatus and the effluent abatement apparatus being in a unitary housing.

In accordance with another aspect of the invention, the ion implantation process system comprises one of the following feature sets:

features (a) and (b);
features (a) and (c);
features (a), (b) and (c);
feature (b); and
features (b) and (c).

of the features:

(a) the supply of source gas including a storage and dispensing vessel containing a physical sorbent medium having the source gas physically adsorbed thereon, with means for dispensing source gas from the vessel by desorbing source gas from the physical sorbent medium and discharging same from the vessel to the ion implanter apparatus;

(b) the effluent abatement apparatus including a dry scrubbing composition for contacting with the effluent gas stream to remove hazardous effluent species therefrom, in which the dry scrubbing composition is selected from the group consisting of the compositions:
(i) $Fe_2O_3$
(ii) $Fe_2O_3$ impregnated with a base;
(iii) $Ca(OH)_2$;
(iv) $Ca(OH)_2$ impregnated with a base;
(v) $Fe_2O_3$ and $MnO_x$, wherein x is from 1 to 2 inclusive;
(vi) $Fe_2O_3$ and $MnO_z$ impregnated with a base, wherein x is from 1 to 2 inclusive;
(vii) CuO and $MnO_x$, wherein x is from 1 to 2 inclusive;
(viii) CuO and $MnO_z$ impregnated with a base, wherein x is from 1 to 2 inclusive;
(ix) CuO, $Al_2O_3$ and $SiO_2$; and
(x) CuO, $Al_2O_3$ and $SiO_2$ impregnated with a base;
wherein the base when present in the scrubbing composition is in a concentration sufficient to enhance the scrubbing capacity of the composition relative to a corresponding composition lacking the impregnated base component, with the base preferably being a strong base, such as KOH, NaOH, LiOH, BaOH, or the like; and (c) the effluent abatement apparatus including at least one bed of a dry scrubbing composition through which the effluent gas stream is flowed to remove hazardous effluent species therefrom, and an end point monitor device operatively associated with each such bed, for determining when the scrubbing capacity of the bed is depleted to a predetermined extent.

As used herein, the scrubbing compositions herein disclosed are intended to be broadly construed, and may alternatively comprise, consist, or consist essentially of the specific stated components or ingredients hereafter specifically identified for such compositions. It will also be understood that such compositions may if desired be devoid of components or ingredients not herein expressly identified.

In a particular aspect, the ion implantation system of the invention may comprise as the aforementioned end point detector device (c) a quartz crystal microbalance arranged with a coating thereon with which an effluent gas stream component to be monitored is interactive to produce a change in frequency response thereof indicative of the end point operation of the bed of dry scrubber composition.

In another aspect of the invention, an ion implant system effluent stream is dry scrubbed to remove acid gas and hydride components thereof, using a dry scrubber composition consisting primarily of CuO and $MnO_x$ wherein x is from 1 to 2 inclusive, and wherein the composition contains from about 15 wt. % to about 40 wt. % CuO and from about 40 wt. % to about 60 wt. % $MnO_x$, based on the total weight of the composition.

Other aspects, features and embodiments will be more fully apparent from the ensuing disclosure and appended claims.

DETAILED DESCRIPTION OF THE INVENTION, AND PREFERRED EMBODIMENTS THEREOF

The system of the present invention provides for delivery of dopant gases to the ion source chamber of an ion implantation apparatus and treatment of the resulting effluent gas stream produced by the ion implantation apparatus, in an integrated and efficient manner.

The system accommodates the collection of unutilized dopant gases in the effluent gas stream by irreversible chemisorption by contacting the effluent gas stream with a chemisorbent scrubber composition, and the continuous monitoring of the chemisorbent scrubber composition to determine the approach to exhaustion of the capacity of the chemisorbent scrubber composition to remove undesired components of the effluent gas stream.

Figure 1:
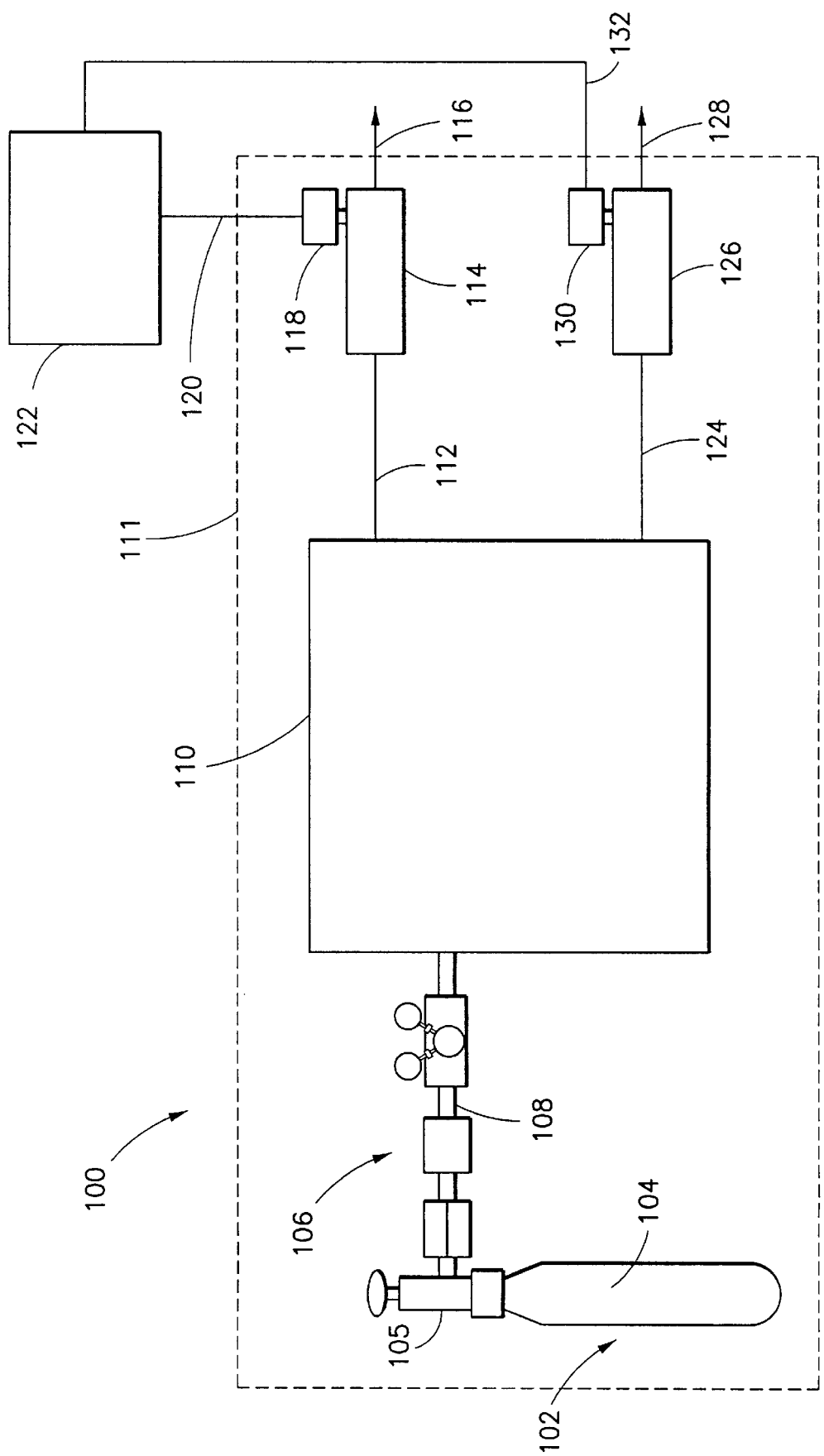
FIG. 1 is a schematic representation of an integrated ion implantation scrubber system according to one embodiment of the invention.

FIG. 1 is a schematic representation of an integrated ion implantation scrubber system 100 according to one embodiment of the invention.

The integrated ion implantation scrubber system 100 includes a feed source 102 of source gas for the ion implantation operation, which may comprise a source gas storage and dispensing vessel 104 of a type as hereinafter described in greater detail in FIG. 2 hereof. The source gas storage and dispensing vessel 104 is constructed to be leak-tight and to hold within its interior volume a physical adsorbent material having sorptive affinity for the dopant gas used in the ion implantation. The vessel 104 is joined to a valve head assembly 105 which in turn is coupled to the gas dispensing manifold assembly 106 including line 108, through which the dispensed gas is flowed to the ion implantation apparatus 110 represented schematically in FIG. 1, but of a type as more fully described hereafter in connection with FIG. 3 hereof.

The dopant gas used in the ion implantation apparatus may for example be arsine gas for ion implantation of $As^+$ in a substrate such as a microelectronic device structure.

The ion implantation apparatus 110 produces an effluent gas stream which is discharged from the ion implantation apparatus in line 112 and passed to the dry scrubber bed 114 for removal therein of contaminant(s) and discharge of a purified effluent gas stream in line 116 to downstream processing or final disposition of same. The dry scrubber bed 114 contains an end point monitor 118, which is coupled by signal transmission line 120 to output module 122 for outputting an indication of breakthrough of the contaminant (s) in the effluent gas stream when the capacity of the scrubber bed for active processing of the effluent gas stream is exhausted or reaches a predetermined approach to exhaustion (e.g., reaches a point of exhaustion of 95% of the total capacity of the dry scrubber material).

The end point monitor may be of any suitable type, as for example an end-point monitor of a general type as disclosed in U.S. Pat. Nos. 5,138,869; 5,325,705; and 5,583,282. In a preferred aspect of the invention, the end-point monitor comprises a quartz microbalance (QMB) detector of a type as more fully described hereafter in connection with FIG. 5 hereof.

Effluent gas from the ion implantation system 110 may also be discharged into a second line 124 and flowed to the scrubber bed 126 for removal of undesired gas stream components therein, to yield a purified gas stream which is discharged from the scrubber bed in line 128 and passed to further treatment or other disposition steps.

An end-point detector 130 is arranged to sense contaminant concentration breakthrough and to responsively generate a signal indicative of such breakthrough which is passed by signal transmission line 132 to output module 122 for outputting an indication of breakthrough of the contaminant (s) in the effluent gas stream, in the same manner as described above for the end point detector 118 associated with scrubber bed 114.

The scrubber beds 114 and 126 may be provided in duplicate as shown, with one of the beds being a backup scrubbing unit, and with the lines 112 and 124 containing suitable valving and instrumentation to accommodate such redundancy function, so that one of the beds is initially on-stream and actively scrubbing the effluent gas stream from the ion implantation apparatus 110, while the other is in stand-by mode.

When a signal indicating breakthrough of contaminant is generated by the end-point detector for the on-stream bed, the effluent gas stream flow is thereupon switched to the stand-by scrubber bed, which then becomes the active processing module while the exhausted scrubber bed is changed out, to replace the scrubber composition therein, or otherwise regenerate the exhausted bed for renewal of active scrubbing operation when the other bed in turn becomes exhausted.

Alternatively, the two scrubber beds 114 and 126 may be concurrently operated, and may each process different effluent streams generated in the operation of the ion implantation apparatus. For example, one of such scrubber beds may process a main effluent gas stream from the ion implantation apparatus, while the other may for example process a minor effluent stream deriving from pump leakage gas in the effluent treatment system.

The scrubber system may be deployed as a separate and distinct apparatus component of the overall system, in relation to the ion implantation apparatus, and the feed source of the ion implantation gas, or alternatively, as shown in FIG. 1, with reference to the dotted line 111 denoting a unitary housing of the ion implanter, the feed source and/or scrubber system may be deployed within the ion implanter itself.

In such manner, the scrubber system may be integrated in a housing containing the ion implanter and associated components (e.g., ionizer unit, ion selection/deselection unit, focusing electrodes, etc.), as a unitary modular system, which has associated therewith an output or display panel (not illustrated in FIG. 1) showing process conditions, as for example ionization voltages, magnetic field strengths, implanter pressure, and breakthrough of contaminant(s) in the scrubber bed as detected by the end-point detector associated therewith.

The breakthrough condition detected by the end-point detector may be outputted in any suitable manner(s), including for example sonic alarms, visual outputs including calorimetric displays, visual indicia (output) data, etc., which signal the need to change out the scrubber composition in the scrubber bed that has been exhausted by on-stream scrubbing use.

By the system shown in FIG. 1, the process gases leaving the ion implanter apparatus, e.g., the ion source chamber, are exhausted to vessel(s) containing a dry scrubbing composition specific to the ion implantation gases to be abated in the effluent gas stream. The dry scrubbing composition removes the waste gases from effluent, e.g., the ion source chamber exhaust, by chemisorption, irreversibly bonding the waste gas species to the scrubbing medium to maximum operator safety and environmental acceptability of the finally discharged process effluent after its scrubbing treatment.

The dry scrubbing composition may therefore be provided in canisters which are deployed in the ionimplanter apparatus to treat the effluent gas stream(s) produced by the process and yield an environmentally acceptable discharged stream. Such canisters can be readily changed out by decoupling same from connecting piping and valving employing conventional connector devices, and replacing the canister of spent scrubber medium with a corresponding canister of fresh medium.

The amount of scrubbing medium used in such disposable canisters for waste gas treatment will be determined by the available dead volume within the ion implanter, when the canisters are interiorly positioned in the implanter system housing, and by the deliverable capacity of the feed source of doping gas for the ion implantation system. The feed source volume may be desirably matched to the system throughput, so that the capacity of the source gas vessel does not exceed the removal capacity of the waste gas abatement canister(s) deployed in the system.

In accordance with a preferred aspect of the invention, each such waste gas treatment canister is fitted with an integral endpoint detector sensor element. The endpoint detector is constructed, operated and arranged to generate an alarm when a predetermined extent, e.g., 90 or 95 percent of the waste gas treatment canister's capacity has been exhausted. The capacity of the treatment canister is most preferably selected (by sizing the canister and using an appropriate scrubbing composition) to exceed the capacity of the feed source for the ion implant dopant gas, so that the endpoint detector serves a redundant, fail-safe function.

In such canister units containing the scrubbing composition, the endpoint detector sensor element associated with the canister preferably is disposable, so that it can be unplugged from the detector's compact control platform during canister changeout procedures, and so that a fresh detector element can be plugged into the control platform when a fresh chemisorption bed canister is installed.

In a preferred embodiment, the detector sensor consists of a solid quartz single crystal, across which an oscillating voltage is applied at a resonant frequency by means of two electrodes. The electrode material may be selected to be reactive with the contaminant gas species of interest, or the crystal may have deposited thereon a coating of a material that is interactive with the contaminant gas species, being either adsorbed thereon, or reactive with the coating to yield a reacted coating of different mass than originally provided.

In all of such cases, the change of mass of the crystal as it is oscillated changes the frequency response of the crystal and is indicative of interaction of the crystal with the gas species of interest, i.e., breakthrough of the gas species of interest. The frequency shift is sensed and the sensing signal may be manipulated by conventional signal processing means and techniques to provide an output indicative of the occurrence of breakthrough.

By way of a specific example, the QMB detector may be arranged and operated to generate an analog 4–20 mA signal, which can be integrated with the host ion implanter unit's other alarm circuits to provide an alarm status alert through the implanter unit's control panel, and the ion implantation unit can be interlocked to shut down the implantation process in the event of a gas breakthrough.

The system of the present invention in such manner integrates safe gas delivery by the provision of a low pressure implantation gas source, waste gas abatement, and real time toxic gas monitoring. By integrating these functions directly into the ion implant tool itself, the need for external gas cabinets, abatement systems and toxic gas monitors, which comprise current practice are eliminated.

Implementation of the integrated system of the invention results in reduced capital cost, substantial reduction in the space required for a fully configured ion implanter installation, and greatly enhanced safety of operation of the implanter, relative to current practice.

Figure 2:
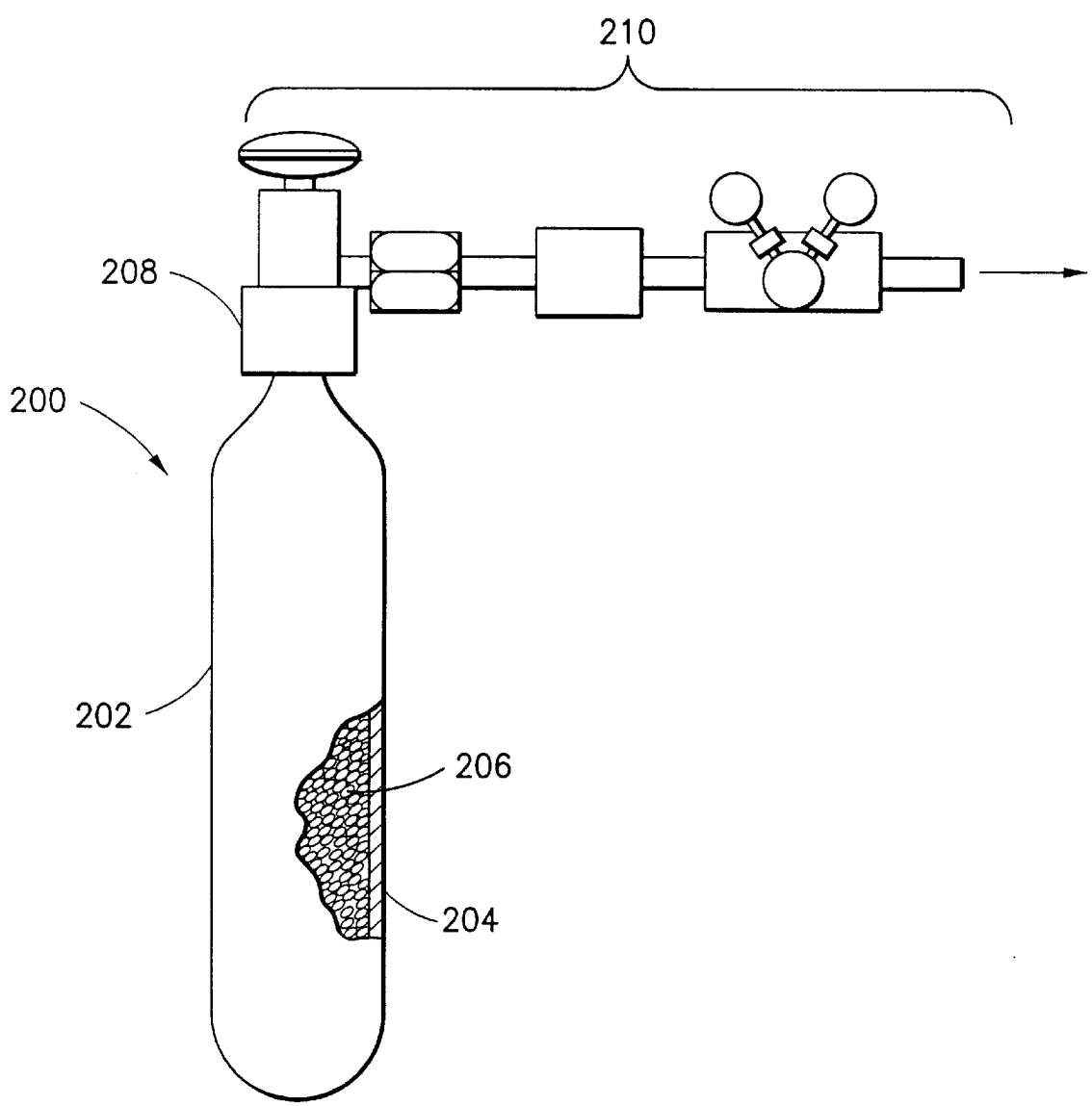
FIG. 2 is a schematic perspective representation of a storage and dispensing vessel and associated flow circuitry according to one embodiment of the invention, which may be usefully employed for the storage and dispensing of source gas to the ion implanter apparatus in the integrated ion implantation scrubber system according to the invention.

FIG. 2 is a schematic representation of a storage and dispensing system 200 comprising storage and dispensing vessel 202. The storage and dispensing vessel may for example comprise a conventional gas cylinder container of elongate character, or other vessel of desired size and shape characteristics. In the interior volume of such vessel bounded by the vessel wall 204 is disposed a bed of a suitable adsorbent medium 206.

The gas for the ion implantation is held on the adsorbent medium by physisorption, at an interior pressure in the vessel which may be on the order of for example from about 10 to about 800 torr, and more preferably from about 20 to about 650 torr. The low interaction energy of the adsorbent with the gas molecules allows for delivery of the gas from the source cylinder to the ion source chamber by pressure differential. Since the pressure differential between the ion source chamber (e.g., $10^{-6}$ torr) and the cylinder (e.g., 650 to 20 torr) is considerable, it is possible to meter the flow from the cylinder to the chamber at rates required for ion implantation (~5 sccm), and to utilize virtually all of the cylinder capacity for gas. Flow may be suitably controlled using high conductance metering valves, thermal mass flow controllers and pressure-based flow controllers.

The vessel 200 is provided at its upper end with a conventional cylinder head fluid dispensing assembly 208 coupled with the main body of the cylinder 202, to allow fluid flow from the interior volume of the cylinder into the dispensing assembly 210.

The vessel 200 may also be provided with internal heating means (not shown) which serve to thermally assist desorption of the sorbate fluid. Preferably, however, the sorbate fluid is at least partially, and most preferably fully, dispensed from the storage and dispensing vessel containing the adsorbed fluid by pressure differential established by flow communication between the storage and dispensing vessel, on the one hand, and the exterior dispensing environment and locus of use, on the other. The dispensing means for the vessel may also be augmented to include pumps, blowers, fans, eductors, ejectors, etc., or any other motive driver to assist in flowing the fluid from the vessel to the locus of use of the dispensed fluid.

The sorbent medium 206 may comprise any suitable sorptively effective material, having sorptive affinity for the fluid to be stored and subsequently dispensed from the vessel 200, and from which the sorbate is suitably desorbable. Examples include crystalline aluminosilicate compositions, e.g., a micropore aluminosilicate composition with a pore size in the range of from about 4 to about 13 Å, mesopore crystalline aluminosilicate compositions with a pore size in the range of from about 20 to about 40 Å, carbon sorbent materials, such as a bead activated carbon sorbent of highly uniform spherical particle shape, e.g., BAC-MP, BAC-LP, and BAC-G-70R bead carbon materials (Kreha Corporation of America, New York, N.Y.), silica, alumina, macroreticulate polymers, kieselguhr, porous silicon, porous teflon, etc.

The sorbent material may be suitably processed or treated to ensure that it is devoid of trace components that may deleteriously affect the performance of the fluid storage and dispensing system. For example, the sorbent may be subjected to washing treatment, e.g., with hydrofluoric acid, to render it sufficiently free of trace components such as metals and oxidic transition metal species, or it may otherwise be heated or processed to ensure the desired purity and/or performance characteristics.

The sorbent may be provided in the form of particles, granules, extrudates, powders, cloth, web materials, honeycomb or other monolithic forms, composites, or other suitable conformations of useful sorbent materials, having sorptive affinity for the fluid to be stored and subsequently dispensed, and with satisfactory desorption characteristics for the dispensing operation.

As mentioned, although it generally is preferred to operate solely by pressure differential at ambient temperature conditions, in respect of the sorption (of the ion implantation gas on the sorbent medium in the initial loading of the storage and dispensing vessel) and desorption of the gas to be subsequently dispensed, the storage and dispensing vessel may in some instances advantageously employ a heater operatively arranged in relation to the storage and dispensing vessel for selective heating of the solid-phase physical sorbent medium, to effect thermally-enhanced desorption of the sorbed fluid from the solid-phase physical sorbent medium.

The storage and dispensing vessel optionally may be constructed with a solid-phase physical sorbent medium being present in the storage and dispensing vessel together with a chemisorbent material having a sorptive affinity for contaminants, e.g., decomposition products, of the sorbate fluid therein.

Figure 3:
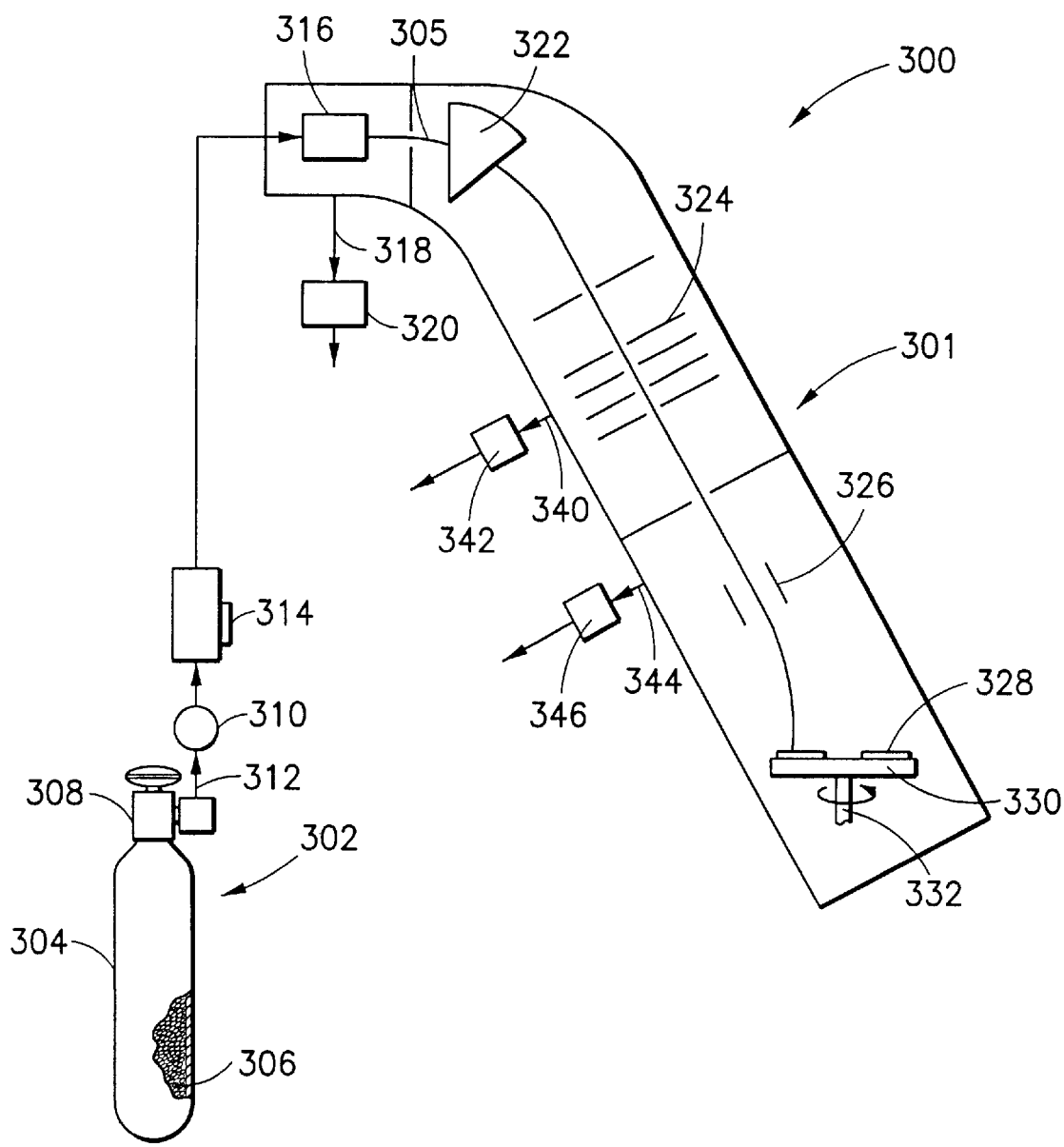
FIG. 3 is a schematic representation of an ion implant process system including a storage and dispensing vessel containing gas which is supplied for ion implantation doping of a substrate in the illustrated ion implant chamber.

FIG. 3 is a schematic representation of an ion implant process system 300 including a storage and dispensing vessel 302 containing a sorbent material 306 in its interior volume holding arsine gas which is supplied for ion implantation doping of a substrate 328 in the illustrated ion implant chamber 301.

The storage and dispensing vessel 302 comprises a vessel wall 304 enclosing an interior volume holding the sorbent material 306, which may be in a bead, particle or other finely divided form, as herein described. A sorbate gas is retained in the interior volume of the vessel on the sorbent material.

The storage and dispensing vessel 302 includes a valve head 308 coupled in gas flow communication with a discharge line 312. A pressure sensor 310 is disposed in the line 312, together with a mass flow controller 314; other monitoring and sensing components may be coupled with the line, and interfaced with control means such as actuators, feedback and computer control systems, cycle timers, etc.

The ion implant chamber 301 contains an ion beam generator or ionizer 316 receiving the dispensed gas, e.g., arsine, from line 312 and generating an ion beam 305. The ion beam 305 passes through the mass analyzer unit 322 which selects the ions needed and rejects the non-selected ions.

The selected ions pass through the acceleration electrode array 324 and then the deflection electrodes 326. The resultingly focused ion beam is impinged on the substrate element 328 disposed on the rotatable holder 330 mounted in turn on spindle 332. The ion beam of $As^+$ ions is used to n-dope the substrate as desired to form an n-doped structure.

The respective sections of the ion implant chamber 301 are exhausted through lines 318, 340 and 344 by means of pumps 320, 342 and 346, respectively.

As discussed, the storage and dispensing system may be integrated with the ion implanter, so that both units are in a unitary installation.

Figure 4:
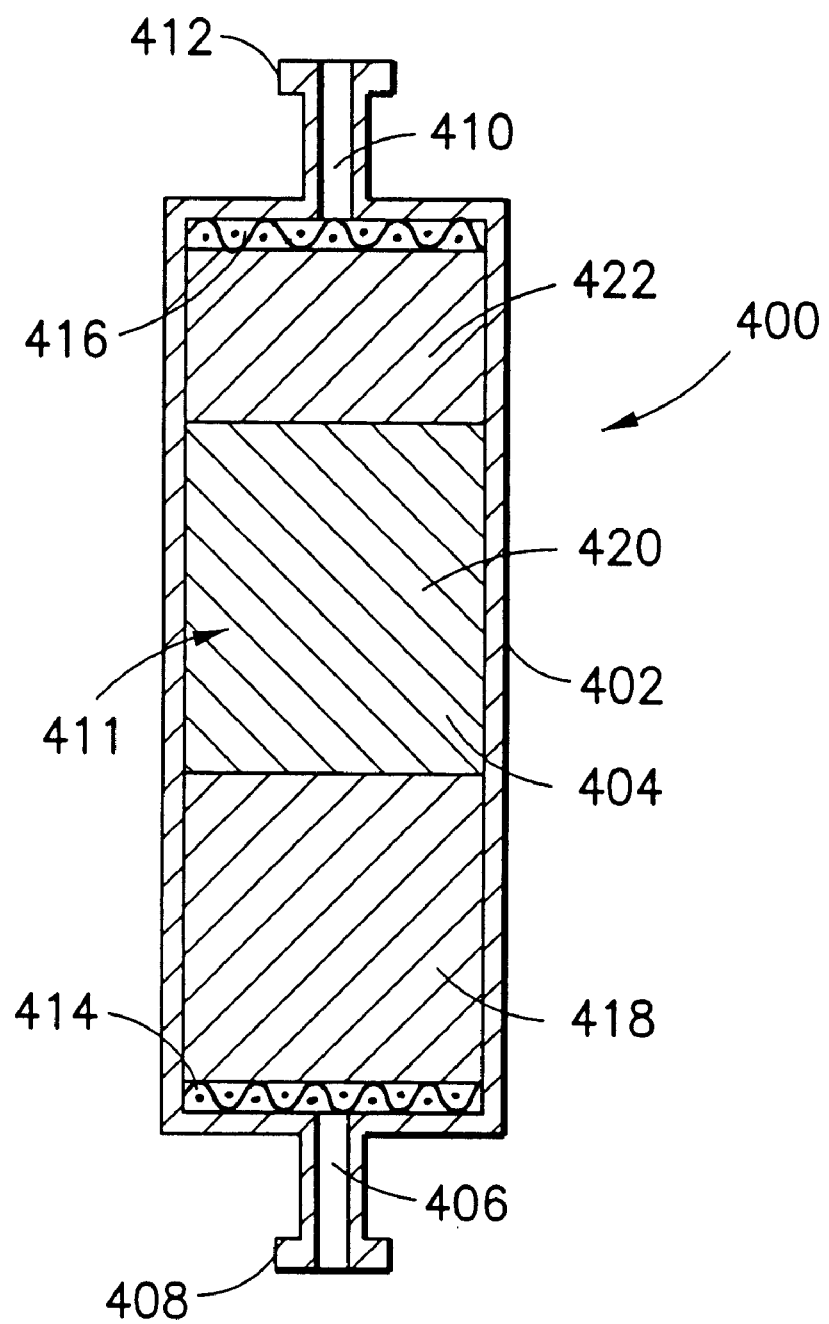
FIG. 4 is a schematic representation of a dry scrubber bed such as may be employed for the treatment of ion implanter effluent gases in accordance with the present invention.

FIG. 4 is a schematic representation of a dry scrubber bed unit 400 such as may be employed for the treatment of ion implanter effluent gases in accordance with the present invention.

The dry scrubber bed unit 400 includes a vessel 402 enclosing an interior vessel volume 404 communicating with the waste gas stream feed passage 406 in inlet 408, and communicating with the scrubbed gas discharge passage 410 in outlet 412. At the respective inlet and outlet ends of the vessel 402 are provided screen or grid members 414 and 416, respectively. These foraminous members serve to contain the bed 411 of scrubbing media in the vessel's interior volume, so that solids attrition does not occur in use of the system as waste gas is flowed from the inlet 406 to outlet 412 of the vessel through the bed of scrubbing media therein.

The bed 411 of scrubbing media may comprise a single homogeneous composition of chemisorbent scrubber material, or as shown in FIG. 4 the bed may comprise a plurality of discrete zones of different scrubbing materials 418, 420 and 422. Alternatively, the scrubbing medium may comprise different scrubber materials which are blended to provide a uniform mixture of same.

Thus, different scrubber materials may be employed, either in discrete bed zones or as components of a blended mixture of scrubbing materials, in which the respective scrubber materials are selective for removal of different waste gas components. For example, one such scrubber material may be highly selective for acid gas components of the effluent gas stream from the ion implanter, and another scrubber material may be highly selective for hydride gas species in the effluent gas stream.

In a preferred compositional embodiment of the present invention, novel scrubbing compositions are employed to provide for concurrent removal of acid gas and hydride gas components of the effluent gas stream, which are based on commercially available materials which have been modified by impregnation thereof with a strong base, such as KOH, LiOH, NaOH, BaOH, or the like.

More specifically, in one compositional aspect, a scrubber material consisting primarily of $Fe_2O_3$ (commercially available from Nissan Girdler as N-600 catalyst) is effective as a scrubber for gas stream components such as $Cl_2$ and $BCl_3$. Impregnation of this material with a strong base, such as KOH, NaOH, LiOH, or BaOH, produces a faster scrubbing material, in which the strong base serves to catalyze the acid/base reaction so that the scrubber as thus modified will initially chemisorb acid gas contaminants of the ion implant waste gas stream. The base will then migrate the contaminant to the lower-basicity $Fe_2O_3$, reverting the base to its "native" condition and conditioning the base to chemisorb additional acid gas contaminants.

Such base impregnation modification can also be applied to other conventionally available scrubber materials, such as: a scrubber material consisting primarily of $Ca(OH)_2$ (commercially available as N-620 catalyst from Nissan Girdler, and as Sofnolime from O. C. Lugo); a scrubber material consisting primarily of $Fe_2O_3$ and $MnO_x$ (commercially available as N-150 catalyst from Nissan Girdler, containing 60% $Fe_2O_3$ and 30% $MnO_x$); a scrubber material consisting primarily of CuO and $MnO_x$ (commercially available as N-140 catalyst from Nissan Girdler, containing 22% CuO and 50% $MnO_x$); and a scrubber material consisting primarily of CuO, $Al_2O_3$ and $SiO_2$ (commercially available as G132D from United Catalysts). By impregnating these commercially available materials with a strong base, such as KOH, a fast acid gas scrubbing composition is produced, having combined hydride and acid gas removal capability.

In the foregoing compositions containing $MnO_x$, x is from 1 to 2 inclusive. Values of x between 1 and 2 may be achieved by non-integer stoichiometric ratios of oxygen to manganese in the scrubber composition, and/or by physical mixtures of MnO and $MnO_2$.

In some instances, it may be feasible to operate with a scrubber material which has not been impregnated with a KOH or other strong base, e.g., if the acid gas component of the effluent gas stream being treated is suitably small and/or the scrubber material has sufficient capacity (measured for example in units of moles of acid gas per liter of scrubber bed) for the acid gas constituents of the effluent gas stream.

One such non-impregnated scrubber composition that may be usefully employed in the broad practice of the invention for concurrent acid gas and hydride gas removal is a scrubber material consisting primarily of CuO and $MnO_x$ (commercially available as N-140 catalyst from Nissan Girdler, containing 22% CuO and 50% $MnO_x$), wherein x is from 1 to 2 inclusive, e.g., from about 1.5 to about 1.7.

Such $CuO/MnO_x$ material, in tests evaluating the removal of arsine and boron trifluoride from gas streams containing same, demonstrated unexpectedly high removal levels of these gas components when used in a dry granular form (for example in 8×14 granules).

The dry state of the CuO/MnO$_x$ scrubber material may be ensured by utilizing the scrubber material in combination with a water removal agent, e.g., in a guard bed of dessicant or water-removing chemisorbent, upstream of the bed of scrubber material, or in a mixed bed of the CuO/MnO$_x$ material and the water removal agent.

The scrubber material may be used in any suitable form, as for example in a bead, granular, or extrudate form. The size, shape and form of the scrubber material may be readily determined within the skill of the art, to determine an optimal set of characteristics for the scrubber material in a given end use application.

Figure 5:
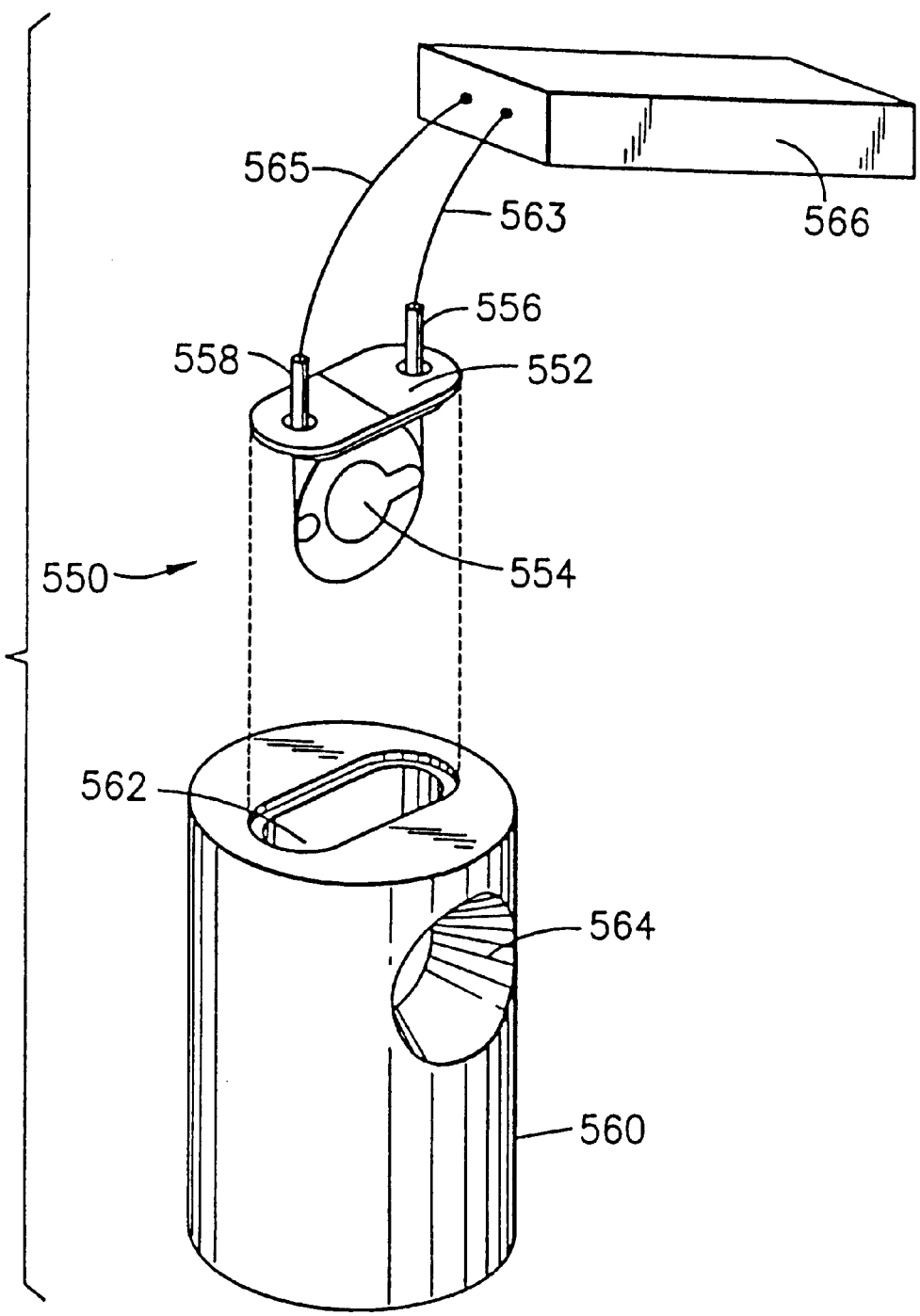
FIG. 5 is a schematic representation of a quartz microbalance device, of a type usefully employed to monitor the endpoint of active processing life of a scrubber composition used for the scrubbing treatment of effluent gas from an ion implantation system of the invention.

FIG. 5 is a schematic representation of a quartz microbalance device, of a type usefully employed to monitor the endpoint of active processing life of a scrubber composition used to scrub effluent gas from an ion implantation system in the practice of the present invention.

FIG. 5 shows an exploded view of a QMB detector according to one embodiment of the invention, comprising the sensor element 550 and the housing 560. The sensor element 550 comprises the piezoelectric crystal 554 which is coated with a suitable material interacting with the fluid component of interest to yield an interaction product of differing mass characteristic than the original coating material. The coated crystal is mounted on the plug member 552, with the respective leads 556 and 558 of the piezoelectric crystal 554 protruding exteriorly of the plug member when the plug member is engaged with the housing 560 with the coated crystal extending into the cavity 562.

The housing 560 features an opening 564 by which a gas can be flowed into the cavity 562 containing the sensor element 550. Although not shown in the front perspective view of FIG. 5, the housing 560 has another opening therein, opposite opening 564 and in register with such opening, for discharge from the housing of the gas flowed past the coated piezoelectric crystal.

The leads 556 and 558 of the sensor element may be coupled in circuit relationship to suitable electronics means shown schematically as electronics module 566 in FIG. 5, by which the presence and concentration of the gas impurity species can be detected. The electronics module 566 is coupled to the sensor element leads 556 and 558 by wires 563 and 565, respectively.

Electronics module 566 provides the functions of (i) sampling the output resonant frequency of the piezoelectric crystal while the oscillating electric field is applied thereto, (ii) determining the change in resonant frequency from the fundamental resonant frequency incident to the formation of the solid interaction product when the sensor material interacts with the contaminant in the effluent gas stream being monitored, and (iii) generating an output indicative of the presence of the contaminant in such effluent gas stream.

In a specific embodiment of the sensor assembly shown in FIG. 5, the housing 560 may comprise an aluminum housing which has the cavity 562 machined into it for insertion of the sensor element, as well as two feedthrough (¼" NPT) openings (opening 562 and the opposite opening not shown in FIG. 5) for the gas to flow through the sensor. In the body of this housing is the flow restricting orifice. This ¼" aluminum housing fits directly on the scrubber vessel and the front end driver electronics are plugged directly onto the legs (leads 556 and 558) of the sensor assembly. The resulting assembly may be coupled to a sensor tube of the scrubber vessel, or otherwise joined in flow sensing communication with the scrubber vessel or scrubber bed therein.

While the invention has been shown and described herein with reference to various illustrative aspects, features and embodiments, it will be appreciated that the utility of the invention is not thus limited, but rather extends to and encompasses other variations, modifications and other embodiments of the invention. The claims hereafter set forth are therefore to be construed and interpreted, as including such other variations, modifications and other embodiments of the invention, within their spirit and scope.

What is claimed is:

1. An ion implantation process system, comprising (a) a supply of source gas for the ion implantation process, joined in flow communication with (b) an ion implanter apparatus, with the ion implanter apparatus discharging an effluent gas stream to (c) a dry scrubber effluent abatement apparatus, for removing hazardous effluent species from the effluent gas stream, wherein (a) and (c) are arranged in an integrated unitary assembly with (b).

2. An ion implantation process system according to claim 1, wherein the source gas supply comprises a storage and dispensing vessel holding a physical adsorbent medium therein sorptively retaining the source gas, with means for dispensing the source gas from the vessel and flowing the dispensed gas to the ion implanter apparatus.

3. An ion implantation process system according to claim 1, wherein two dry scrubber effluent abatement apparatuses are positioned in the ion implanter apparatus as a unitary and integrated process arrangement.

4. An ion implantation process system according to claim 1, wherein the effluent abatement apparatus comprises a canister containing a bed of chemisorbent material which is reactive with at least one component of the effluent gas stream discharged from the ion implanter apparatus, and the canister is contained in a dead space volume of the ion implanter apparatus and arranged for flow of the effluent gas stream therethrough.

5. An ion implantation process system according to claim 4, wherein the canister has an associated endpoint detector device for determining an approach to exhaustion of capacity of the chemisorbent material in treatment of the effluent gas stream flowed through the canister.

6. An ion implantation process system according to claim 1, wherein the effluent abatement apparatus comprises a quartz crystal microbalance interactive with at least one component of the effluent gas stream to produce a change in the oscillation frequency of the quartz crystal microbalance indicative of breakthrough of said component during flow of the effluent gas stream therethrough.

7. An ion implantation process system according to claim 1, wherein the effluent abatement apparatus comprises a chemisorbent composition capable of chemisorbing both acid gas components and hydride gas components of the effluent gas stream.

8. An ion implantation process system according to claim 1, wherein the effluent abatement apparatus comprises a chemisorbent composition selected from the group consisting of the compositions:

(i) $Fe_2O_3$
(ii) $Fe_2O_3$ impregnated with a base;
(iii) $Ca(OH)_2$;
(iv) $Ca(OH)_2$ impregnated with a base;
(v) $Fe_2O_3$ and $MnO_x$, wherein x is from 1 to 2 inclusive;
(vi) $Fe_2O_3$ and $MnO_z$ impregnated with a base, wherein x is from 1 to 2 inclusive;
(vii) CuO and $MnO_x$, wherein x is from 1 to 2 inclusive;
(viii) CuO and $MnO_z$ impregnated with a base, wherein x is from 1 to 2 inclusive;

(ix) CuO, $Al_2O_3$ and $SiO_2$; and
(x) CuO, $Al_2O_3$ and $SiO_2$ impregnated with a base;
wherein the base when present in the scrubbing composition is in a concentration sufficient to enhance the scrubbing capacity of the composition relative to a corresponding composition lacking the impregnated base component.

9. An ion implantation process system according to claim 8, wherein the base is selected from the group consisting of KOH, BaOH, LiOH, NaOH, and mixtures of two or more of the foregoing species.

10. An ion implantation process system according to claim 1, wherein the dry scrubber effluent abatement apparatus comprises a chemisorbent composition selected from the group consisting of the compositions:
(i) $Fe_2O_3$
(ii) $Fe_2O_3$ impregnated with a base;
(iii) $Ca(OH)_2$;
(iv) $Ca(OH)_2$ impregnated with a base;
(v) $Fe_2O_3$ and $MnO_x$, wherein x is from 1 to 2 inclusive;
(vi) $Fe_2O_3$ and $MnO_z$ impregnated with a base, wherein x is from 1 to 2 inclusive;
(vii) CuO, $Al_2O_3$ and $SiO_2$; and
(viii) CuO, $Al_2O_3$ and $SiO_2$ impregnated with a base.

11. An integrated ion implantation process system comprising an ion implantation source gas supply, an ion implanter apparatus arranged in gas-receiving relationship to the ion implantation source gas supply, said ion implanter apparatus producing an effluent gas stream, and a dry scrubber effluent abatement apparatus for removing at least one component of the effluent gas stream and an end point monitor device operatively associated with the dry scrubber, wherein the ion implantation source gas supply, the ion implanter apparatus and the dry scrubber effluent abatement apparatus being in a unitary housing.

12. An ion implantation process system, comprising:
an ion implanter apparatus for carrying out an ion implantation process;
a supply of source gas for the ion implantation process, joined in flow communication with the ion implanter apparatus, and with the ion implanter apparatus discharging an effluent gas stream including ionization products of the source gas during the ion implantation process; and
a dry scrubber effluent abatement apparatus for removing hazardous effluent species from the effluent gas stream
wherein the ion implantation process system comprises one of the following feature sets:
features (a) and (b);
features (a) and (c);
features (a), (b) and (c);
feature (b); and
features (b) and (c);
of the features:
(a) the supply of source gas including a storage and dispensing vessel containing a physical sorbent medium having the source gas physically adsorbed thereon, with means for dispensing source gas from the vessel by desorbing source gas from the physical sorbent medium and discharging same from the vessel to the ion implanter apparatus;
(b) the effluent abatement apparatus including a dry scrubbing composition for contacting with the effluent gas stream to remove hazardous effluent species therefrom, in which the dry scrubbing composition is selected from the group consisting of the compositions:
(i) $Fe_2O_3$
(ii) $Fe_2O_3$ impregnated with a base;
(iii) $Ca(OH)_2$;
(iv) $Ca(OH)_2$ impregnated with a base;
(v) $Fe_2O_3$ and $MnO_x$, wherein x is from 1 to 2 inclusive;
(vi) $Fe_2O_3$ and $MnO_z$ impregnated with a base, wherein x is from 1 to 2 inclusive;
(vii) CuO and $MnO_x$, wherein x is from 1 to 2 inclusive;
(viii) CuO and $MnO_z$ impregnated with a base, wherein x is from 1 to 2 inclusive;
(ix) CuO, $Al_2O_3$ and $SiO_2$; and
(x) CuO, $Al_2O_3$ and $SiO_2$ impregnated with a base;
wherein the base when present in the scrubbing composition is in a concentration sufficient to enhance the scrubbing capacity of the composition relative to a corresponding composition lacking the impregnated base component; and
(c) the effluent abatement apparatus including at least one bed of a dry scrubbing composition through which the effluent gas stream is flowed to remove hazardous effluent species therefrom, and an end point monitor device operatively associated with each such bed, for determining when the scrubbing capacity of the bed is depleted to a predetermined extent.

13. An ion implantation process system according to claim 12, wherein the base is selected from the group consisting of KOH, NaOH, LiOH, and BaOH.

14. An ion implantation process system according to claim 12, comprising as the end point detector device (c) a quartz crystal microbalance arranged with a coating thereon with which an effluent gas stream component to be monitored is interactive to produce a change in frequency response thereof indicative of the end point operation of the bed of dry scrubber composition.

15. An ion implantation process system, comprising:
an ion implanter apparatus for carrying out an ion implantation process;
a supply of source gas for the ion implantation process, joined in flow communication with the ion implanter apparatus, and with the ion implanter apparatus discharging an effluent gas stream including ionization products of the source gas during the ion implantation process; and
a dry scrubber effluent abatement apparatus for removing hazardous effluent species from the effluent gas stream
wherein:
(a) the supply of source gas includes a storage and dispensing vessel containing a physical sorbent medium having the source gas physically adsorbed thereon, with means for dispensing source gas from the vessel by desorbing source gas from the physical sorbent medium and discharging same from the vessel to the ion implanter apparatus; and
(b) the effluent abatement apparatus includes a dry scrubbing composition for contacting with the effluent gas stream to remove hazardous effluent species therefrom, in which the dry scrubbing composition is selected from the group consisting of the compositions:
(i) $Fe_2O_3$
(ii) $Fe_2O_3$ impregnated with a base;
(iii) $Ca(OH)_2$;
(iv) $Ca(OH)_2$ impregnated with a base;

(v) $Fe_2O_3$ and $MnO_x$, wherein x is from 1 to 2 inclusive;
(vi) $Fe_2O_3$ and $MnO_z$ impregnated with a base, wherein x is from 1 to 2 inclusive;
(vii) CuO and $MnO_x$, wherein x is from 1 to 2 inclusive;
(viii) CuO and $MnO_z$ impregnated with a base, wherein x is from 1 to 2 inclusive;
(ix) CuO, $Al_2O_3$ and $SiO_2$; and
(x) CuO, $Al_2O_3$ and $SiO_2$ impregnated with a base;
wherein the base when present in the scrubbing composition is in a concentration sufficient to enhance the scrubbing capacity of the composition relative to a corresponding composition lacking the impregnated base component.

16. An ion implantation process system, comprising:
an ion implanter apparatus for carrying out an ion implantation process;
a supply of source gas for the ion implantation process, joined in flow communication with the ion implanter apparatus, and with the ion implanter apparatus discharging an effluent gas stream including ionization products of the source gas during the ion implantation process; and
a dry scrubber effluent abatement apparatus for removing hazardous effluent species from the effluent gas stream wherein:
  (a) the supply of source gas includes a storage and dispensing vessel containing a physical sorbent medium having the source gas physically adsorbed thereon, with means for dispensing source gas from the vessel by desorbing source gas from the physical sorbent medium and discharging same from the vessel to the ion implanter apparatus;
  (b) the effluent abatement apparatus includes a dry scrubbing composition for contacting with the effluent gas stream to remove hazardous effluent species therefrom, in which the dry scrubbing composition is selected from the group consisting of the compositions:
    (i) $Fe_2O_3$
    (ii) $Fe_2O_3$ impregnated with a base;
    (iii) $Ca(OH)_2$;
    (iv) $Ca(OH)_2$ impregnated with a base;
    (v) $Fe_2O_3$ and $MnO_x$, wherein x is from 1 to 2 inclusive;
    (vi) $Fe_2O_3$ and $MnO_z$ impregnated with a base, wherein x is from 1 to 2 inclusive;
    (vii) CuO and $MnO_x$, wherein x is from 1 to 2 inclusive;
    (viii) CuO and $MnO_z$ impregnated with a base, wherein x is from 1 to 2 inclusive;
    (ix) CuO, $Al_2O_3$ and $SiO_2$; and
    (x) CuO, $Al_2O_3$ and $SiO_2$ impregnated with a base;
  wherein the base when present in the scrubbing composition is in a concentration sufficient to enhance the scrubbing capacity of the composition relative to a corresponding composition lacking the impregnated base component; and
  (c) the effluent abatement apparatus includes at least one bed of a dry scrubbing composition through which the effluent gas stream is flowed to remove hazardous effluent species therefrom, and an end point monitor device operatively associated with each such bed, for determining when the scrubbing capacity of the bed is depleted to a predetermined extent.

17. An ion implantation process system, comprising:
an ion implanter apparatus for carrying out an ion implantation process;
a supply of source gas for the ion implantation process, joined in flow communication with the ion implanter apparatus, and with the ion implanter apparatus discharging an effluent gas stream including ionization products of the source gas during the ion implantation process; and
a dry scrubber effluent abatement apparatus for removing hazardous effluent species from the effluent gas stream,
wherein the effluent abatement apparatus includes a dry scrubbing composition for contacting with the effluent gas stream to remove hazardous effluent species therefrom, in which the dry scrubbing composition is selected from the group consisting of the compositions:
  (i) $Fe_2O_3$
  (ii) $Fe_2O_3$ impregnated with a base;
  (iii) $Ca(OH)_2$;
  (iv) $Ca(OH)_2$ impregnated with a base;
  (v) $Fe_2O_3$ and $MnO_x$, wherein x is from 1 to 2 inclusive;
  (vi) $Fe_2O_3$ and $MnO_z$ impregnated with a base, wherein x is from 1 to 2 inclusive;
  (vii) CuO and $MnO_x$, wherein x is from 1 to 2 inclusive;
  (viii) CuO and $MnO_z$ impregnated with a base, wherein x is from 1 to 2 inclusive;
  (ix) CuO, $Al_2O_3$ and $SiO_2$; and
  (x) CuO, $Al_2O_3$ and $SiO_2$ impregnated with a base;
wherein the base when present in the scrubbing composition is in a concentration sufficient to enhance the scrubbing capacity of the composition relative to a corresponding composition lacking the impregnated base component.

18. An ion implantation process system, comprising:
an ion implanter apparatus for carrying out an ion implantation process;
a supply of source gas for the ion implantation process, joined in flow communication with the ion implanter apparatus, and with the ion implanter apparatus discharging an effluent gas stream including ionization products of the source gas during the ion implantation process; and
a dry scrubber effluent abatement apparatus for removing hazardous effluent species from the effluent gas stream wherein:
  the effluent abatement apparatus includes a dry scrubbing composition for contacting with the effluent gas stream to remove hazardous effluent species therefrom, in which the dry scrubbing composition is selected from the group consisting of the compositions:
    (i) $Fe_2O_3$.

19. An ion implantation process system, comprising:
an ion implanter apparatus for carrying out an ion implantation process;
a supply of source gas for the ion implantation process, joined in flow communication with the ion implanter apparatus, and with the ion implanter apparatus discharging an effluent gas stream including ionization products of the source gas during the ion implantation process; and
a dry scrubber effluent abatement apparatus for removing hazardous effluent species from the effluent gas stream
wherein the ion implantation process system comprises one of the following feature sets:

features (a) and (b);
features (a) and (c);
features (a), (b) and (c);
feature (b); and
features (b) and (c);
of the features:
  (a) the supply of source gas including a storage and dispensing vessel containing a physical sorbent medium having the source gas physically adsorbed thereon, with means for dispensing source gas from the vessel by desorbing source gas from the physical sorbent medium and discharging same from the vessel to the ion implanter apparatus;
  (b) the effluent abatement apparatus including a dry scrubbing composition for contacting with the effluent gas stream to remove hazardous effluent species therefrom, in which the dry scrubbing composition is selected from the group consisting of the compositions:
    (i) $Fe_2O_3$
    (ii) $Fe_2O_3$ impregnated with a base;
    (iii) $Ca(OH)_2$;
    (iv) $Ca(OH)_2$ impregnated with a base;
    (v) $Fe_2O_3$ and $MnO_x$, wherein x is from 1 to 2 inclusive;
    (vi) $Fe_2O_3$ and $MnO_z$ impregnated with a base, wherein x is from 1 to 2 inclusive;
    (vii) $CuO$, $Al_2O_3$ and $SiO_2$; and
    (viii) $CuO$, $Al_2O_3$ and $SiO_2$ impregnated with a base;
  wherein the base when present in the scrubbing composition is in a concentration sufficient to enhance the scrubbing capacity of the composition relative to a corresponding composition lacking the impregnated base component; and
  (c) the effluent abatement apparatus including at least one bed of a dry scrubbing composition through which the effluent gas stream is flowed to remove hazardous effluent species therefrom, and an end point monitor device operatively associated with each such bed, for determining when the scrubbing capacity of the bed is depleted to a predetermined extent.

20. An ion implantation process system, comprising:
an ion implanter apparatus for carrying out an ion implantation process;
a supply of source gas for the ion implantation process, joined in flow communication with the ion implanter apparatus, and with the ion implanter apparatus discharging an effluent gas stream including ionization products of the source gas during the ion implantation process; and
a dry scrubber effluent abatement apparatus for removing hazardous effluent species from the effluent gas stream wherein:
  (a) the supply of source gas includes a storage and dispensing vessel containing a physical sorbent medium having the source gas physically adsorbed thereon, with means for dispensing source gas from the vessel by desorbing source gas from the physical sorbent medium and discharging same from the vessel to the ion implanter apparatus; and
  (b) the effluent abatement apparatus includes a dry scrubbing composition for contacting with the effluent gas stream to remove hazardous effluent species therefrom, in which the dry scrubbing composition is selected from the group consisting of the compositions:
    (i) $Fe_2O_3$
    (ii) $Fe_2O_3$ impregnated with a base;
    (iii) $Ca(OH)_2$;
    (iv) $Ca(OH)_2$ impregnated with a base;
    (v) $Fe_2O_3$ and $MnO_x$, wherein x is from 1 to 2 inclusive;
    (vi) $Fe_2O_3$ and $MnO_z$ impregnated with a base, wherein x is from 1 to 2 inclusive;
    (vii) $CuO$, $Al_2O_3$ and $SiO_2$; and
    (viii) $CuO$, $Al_2O_3$ and $SiO_2$ impregnated with a base;
  wherein the base when present in the scrubbing composition is in a concentration sufficient to enhance the scrubbing capacity of the composition relative to a corresponding composition lacking the impregnated base component.

21. An ion implantation process system, comprising:
an ion implanter apparatus for carrying out an ion implantation process;
a supply of source gas for the ion implantation process, joined in flow communication with the ion implanter apparatus, and with the ion implanter apparatus discharging an effluent gas stream including ionization products of the source gas during the ion implantation process; and
a dry scrubber effluent abatement apparatus for removing hazardous effluent species from the effluent gas stream wherein:
  (a) the supply of source gas includes a storage and dispensing vessel containing a physical sorbent medium having the source gas physically adsorbed thereon, with means for dispensing source gas from the vessel by desorbing source gas from the physical sorbent medium and discharging same from the vessel to the ion implanter apparatus;
  (b) the effluent abatement apparatus includes a dry scrubbing composition for contacting with the effluent gas stream to remove hazardous effluent species therefrom, in which the dry scrubbing composition is selected from the group consisting of the compositions:
    (i) $Fe_2O_3$
    (ii) $Fe_2O_3$ impregnated with a base;
    (iii) $Ca(OH)_2$;
    (iv) $Ca(OH)_2$ impregnated with a base;
    (v) $Fe_2O_3$ and $MnO_x$, wherein x is from 1 to 2 inclusive;
    (vi) $Fe_2O_3$ and $MnO_z$ impregnated with a base, wherein x is from 1 to 2 inclusive;
    (vii) $CuO$, $Al_2O_3$ and $SiO_2$; and
    (viii) $CuO$, $Al_2O_3$ and $SiO_2$ impregnated with a base;
  wherein the base when present in the scrubbing composition is in a concentration sufficient to enhance the scrubbing capacity of the composition relative to a corresponding composition lacking the impregnated base component; and
  (c) the effluent abatement apparatus includes at least one bed of a dry scrubbing composition through which the effluent gas stream is flowed to remove hazardous effluent species therefrom, and an end point monitor device operatively associated with each such bed, for determining when the scrubbing capacity of the bed is depleted to a predetermined extent.

22. An ion implantation process system, comprising:
an ion implanter apparatus for carrying out an ion implantation process;

a supply of source gas for the ion implantation process, joined in flow communication with the ion implanter apparatus, and with the ion implanter apparatus discharging an effluent gas stream including ionization products of the source gas during the ion implantation process; and a dry scrubber effluent abatement apparatus for removing hazardous effluent species from the effluent gas stream, wherein the effluent abatement apparatus includes a dry scrubbing composition for contacting with the effluent gas stream to remove hazardous effluent species therefrom, in which the dry scrubbing composition is selected from the group consisting of the compositions:
(i) $Fe_2O_3$
(ii) $Fe_2O_3$ impregnated with a base;
(iii) $Ca(OH)_2$;
(iv) $Ca(OH)_2$ impregnated with a base;
(v) $Fe_2O_3$ and $MnO_x$, wherein x is from 1 to 2 inclusive;
(vi) $Fe_2O_3$ and $MnO_z$ impregnated with a base, wherein x is from 1 to 2 inclusive;
(vii) CuO, $Al_2O_3$ and $SiO_2$; and
(viii) CuO, $Al_2O_3$ and $SiO_2$ impregnated with a base;

wherein the base when present in the scrubbing composition is in a concentration sufficient to enhance the scrubbing capacity of the composition relative to a corresponding composition lacking the impregnated base component.

23. An ion implantation process system, comprising:

an ion implanter apparatus for carrying out an ion implantation process;

a supply of source gas for the ion implantation process, joined in flow communication with the ion implanter apparatus, and with the ion implanter apparatus discharging an effluent gas stream including ionization products of the source gas during the ion implantation process; and a dry scrubber effluent abatement apparatus for removing hazardous effluent species from the effluent gas stream wherein:

the effluent abatement apparatus includes a dry scrubbing composition for contacting with the effluent gas stream to remove hazardous effluent species therefrom, in which the dry scrubbing composition is selected from the group consisting of the compositions:
(i) $Fe_2O_3$
(ii) $Fe_2O_3$ impregnated with a base;
(iii) $Ca(OH)_2$;
(iv) $Ca(OH)_2$ impregnated with a base;
(v) $Fe_2O_3$ and $MnO_x$, wherein x is from 1 to 2 inclusive;
(vi) $Fe_2O_3$ and $MnO_z$ impregnated with a base, wherein x is from 1 to 2 inclusive;
(vii) CuO, $Al_2O_3$ and $SiO_2$; and
(viii) CuO, $Al_2O_3$ and $SiO_2$ impregnated with a base;

wherein the base when present in the scrubbing composition is in a concentration sufficient to enhance the scrubbing capacity of the composition relative to a corresponding composition lacking the impregnated base component; and the effluent abatement apparatus includes at least one bed of a dry scrubbing composition through which the effluent gas stream is flowed to remove hazardous effluent species therefrom, and an end point monitor device operatively associated with each such bed, for determining when the scrubbing capacity of the bed is depleted to a predetermined extent.

* * * * *